US010828444B2

United States Patent
Albanese et al.

(10) Patent No.: US 10,828,444 B2
(45) Date of Patent: Nov. 10, 2020

(54) SIMULTANEOUS ESTIMATION OF RESPIRATORY PARAMETERS BY REGIONAL FITTING OF RESPIRATORY PARAMETERS

(71) Applicant: KONINKLIJKE PHILIPS N.V., Eindhoven (NL)

(72) Inventors: Antonio Albanese, New York, NY (US); Francesco Vicario, Boston, MA (US); Dong Wang, Cambridge, MA (US); Nikolaos Karamolegkos, New York, NY (US); Nicolas Wadih Chbat, White Plains, NY (US)

(73) Assignee: Koninklijke Philips N.V., Eindhoven (NL)

( * ) Notice: Subject to any disclaimer, the term of this patent is extended or adjusted under 35 U.S.C. 154(b) by 488 days.

(21) Appl. No.: 15/546,774

(22) PCT Filed: Jan. 12, 2016

(86) PCT No.: PCT/IB2016/050115
§ 371 (c)(1),
(2) Date: Jul. 27, 2017

(87) PCT Pub. No.: WO2016/128846
PCT Pub. Date: Aug. 18, 2016

(65) Prior Publication Data
US 2018/0001041 A1    Jan. 4, 2018

Related U.S. Application Data

(60) Provisional application No. 62/115,182, filed on Feb. 12, 2015.

(51) Int. Cl.
*A61M 16/00* (2006.01)
*A61B 5/085* (2006.01)
(Continued)

(52) U.S. Cl.
CPC .......... *A61M 16/024* (2017.08); *A61B 5/085* (2013.01); *A61B 5/087* (2013.01); *A61B 5/4836* (2013.01);
(Continued)

(58) Field of Classification Search
CPC .......... A61M 16/026; A61M 2230/46; A61M 2230/60; A61B 5/085; A61B 5/7239
See application file for complete search history.

(56) References Cited

U.S. PATENT DOCUMENTS 7,322,937 B2 *  1/2008  Blomberg .......... A61M 16/024
                                                    600/538
7,484,508 B2    2/2009  Younes
(Continued)

FOREIGN PATENT DOCUMENTS

JP        2008000436 A      1/2008

OTHER PUBLICATIONS

Antonio Albanese: "Physiology-based Mathematical Models for the Intensive Care Unit: Application to Mechanical Ventilation", Jan. 1, 2014 XP055332137, ISBN: 978-1-303-94555-7 (Year: 2014)*
(Continued)

*Primary Examiner* — Timothy A Stanis
*Assistant Examiner* — Thao Tran
(74) *Attorney, Agent, or Firm* — Daniel H. Brean

(57) ABSTRACT

A medical ventilator (10) performs a method including: receiving measurements of pressure of air inspired by or expired from a ventilated patient (12) operatively connected with the medical ventilator; receiving measurements of air flow into or out of the ventilated patient operatively connected with the medical ventilator; dividing a breath time interval into a plurality of fitting regions (60); and simultaneously estimating respiratory system's resistance and compliance or elastance, and respiratory muscle pressure in each (Continued)

Figure 2:
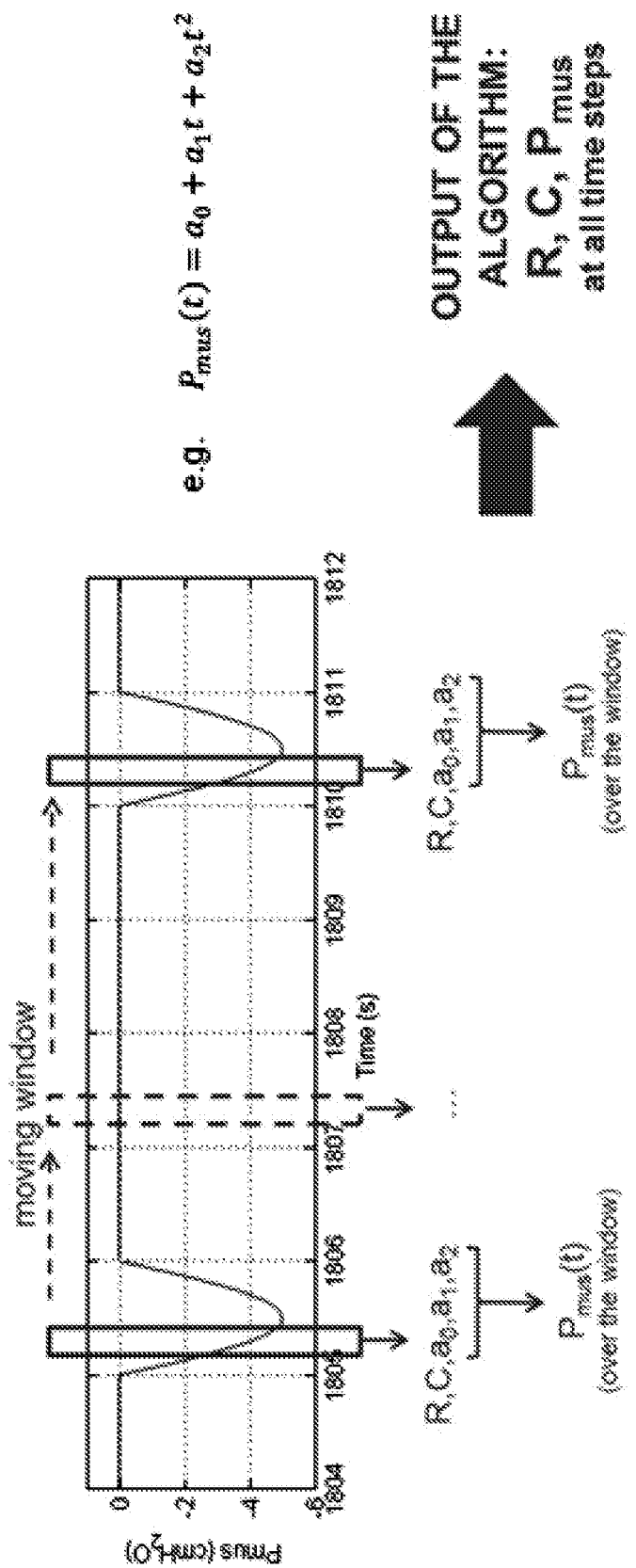

fitting region by fitting to a time series of pressure and air flow samples in that fitting region. In one approach, the fitting includes parameterizing the respiratory muscle pressure by a continuous differentiable function, such as a polynomial function, over the fitting region. In another approach, the fitting is to an equation of motion of the lungs in each fitting region, while monotonicity constraints and inequalities bounding at least the respiratory muscle pressure $P_{mus}(t)$ and respiratory system's resistance R and compliance C are applied to the respiratory muscle pressure in each region.

18 Claims, 10 Drawing Sheets

(51) Int. Cl.
    *A61B 5/087*     (2006.01)
    *A61B 5/00*     (2006.01)
    *G06F 19/00*     (2018.01)
    *G16H 40/63*     (2018.01)

(52) U.S. Cl.
    CPC ...... *A61M 16/0063* (2014.02); *A61M 16/026* (2017.08); *A61M 2016/0027* (2013.01); *A61M 2016/0036* (2013.01); *A61M 2205/3331* (2013.01); *A61M 2205/3334* (2013.01); *A61M 2205/50* (2013.01); *A61M 2230/46* (2013.01); *G06F 19/3481* (2013.01); *G16H 40/63* (2018.01)

(56) References Cited

U.S. PATENT DOCUMENTS

| | | | | |
|---|---|---|---|---|
| 2003/0010339 | A1* | 1/2003 | Banner | ............... A61M 16/026 128/204.18 |
| 2003/0159695 | A1* | 8/2003 | Younes | ............... A61M 16/026 128/204.18 |
| 2009/0022192 | A1 | 1/2009 | Itoh et al. | |
| 2009/0221926 | A1 | 9/2009 | Younes | |
| 2010/0071696 | A1 | 3/2010 | Jafari | |
| 2010/0081119 | A1* | 4/2010 | Jafari | ................... G09B 23/288 434/272 |
| 2011/0237970 | A1 | 9/2011 | Isaza | |
| 2013/0152934 | A1* | 6/2013 | Mulqueeny | ......... A61M 16/026 128/204.23 |
| 2015/0314090 | A1* | 11/2015 | Wu | ..................... A61M 16/021 128/202.22 |

OTHER PUBLICATIONS

Werner Nikischin, Tilo Gerhardt, Ruth Everett, and Eduardo Bancalari,"A New Method to Analyze Lung Compliance When Pressure—Volume Relationship is Nonlinea", 1998 (Year: 1998).*

Brochard et al: "Insiratory Pressure Support Prevents Diaphragmatic Fatigue During Weaning From Mechanical Ventilation"; Am. Rev. Respier. Dis. vol. 139, pp. 513-521, 1989.

Iotti et al:"Noninvasive Evaluation of Instantaneous Total Mechanical Activity of the Respiratory Activity of the Respiratory Muscles During Pressure Support Ventilation"; Chest, vol. 108 (1):208-215, 1995.

Heyer et al: "Non-Invasive Detection of Respiratory Muscles Activity During Assisted Ventilation"; C.R. Biologies 325 (4), pp. 383-391, 2002.

Kondili et al: "Estimatin of Inspiratory Muscle Pressure in Critically Ill Patients"; Intensive Care Med (2010), vol. 36(4), pp. 648-655, 2010.

Lutchen et al: "Optimal Ventilation Waveforms for Estimating Low-Frequency Respiratory Impedance"; J. Appl. Physiology, vol. 75, pp. 478-488, 1993.

Schott et al: "Real-Time Computation of a Patient's Respiratory Effort During Ventilation"; Journal of Clinical Monitoring and Computing (2006), vol. 20, pp. 193-200.

Yamada et al: "Respiratory Muscle Pressure Analysis in Pressure-Support Ventilation"; J. Appl, Physiol, vol. 77(5), pp. 2237-2243, 1994.

Younes et al: "A Method for Monitoring and Improving Patient:Ventilator Interaction"; Intensive Care Med, (2007), vol. 33, pp. 1337-1346.

* cited by examiner

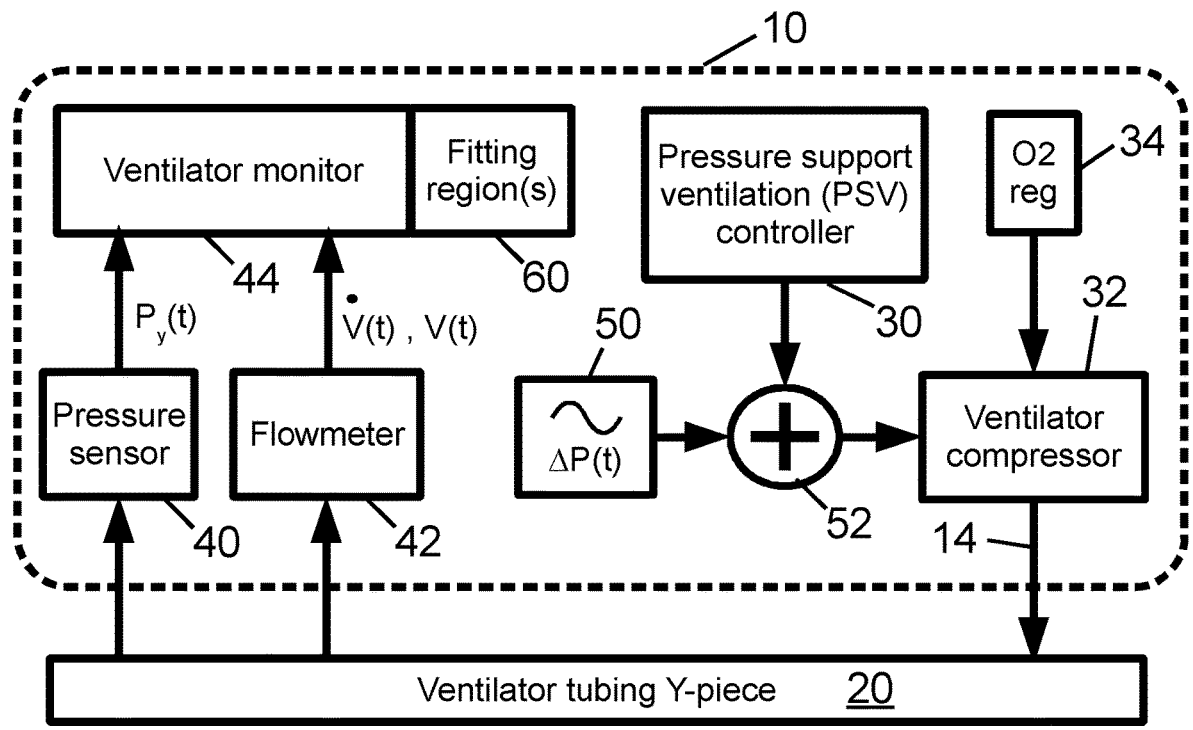
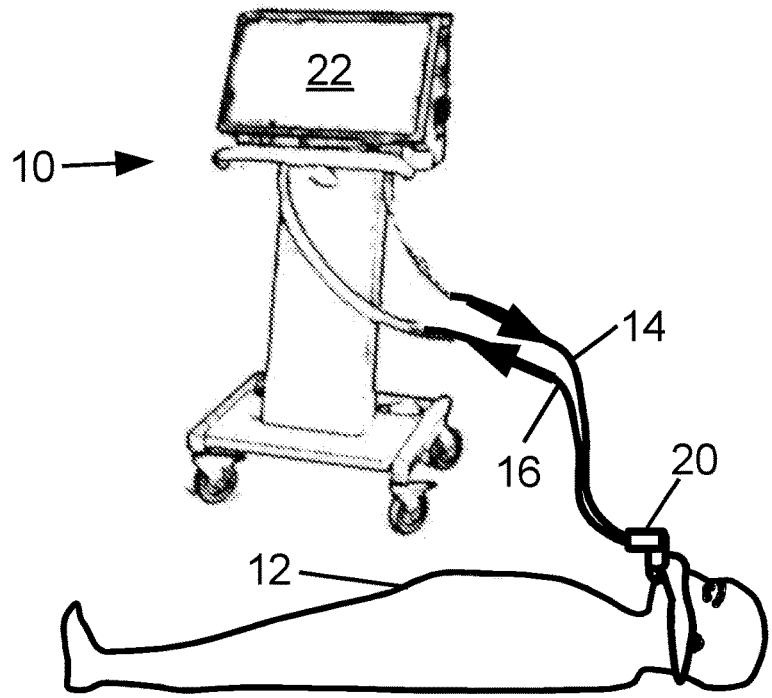
Fig. 1

SIMULTANEOUS ESTIMATION OF RESPIRATORY PARAMETERS BY REGIONAL FITTING OF RESPIRATORY PARAMETERS

CROSS-REFERENCE TO PRIOR APPLICATIONS

This application is the U.S. National Phase application under 35 U.S.C. § 371 of International Application No. PCT/IB2016/050115, filed on Jan. 12, 2016, which claims the benefit of U.S. Provisional Patent Application No. 62/115,182, filed on Feb. 12, 2015. These applications are hereby incorporated by reference herein.

The following relates to the respiratory therapy arts, respiratory monitoring arts, and related arts.

Various types of respiratory therapy employ a mechanical ventilator. In passive patient therapy, the patient is unable to breathe, and the ventilator operates in a pressure control mode in which the ventilator performs the entire work of breathing (WoB). In active patient therapy, the patient can perform some of the necessary work but cannot meet the respiratory demands independently. Thus, ventilator operates in a pressure support mode to provide sufficient pressure to overcome any deficiency in the patient's ability to breathe. Volume control modes of ventilator operation are also known, in which flow rate or volume is the controlled parameter, rather than controlling pressure (although pressure limit settings may also be applied to guard against pulmonary barotrauma), and are mainly used for passive patient therapy.

In determining ventilator settings and subsequent monitoring of a mechanically ventilated patient, it may be advantageous to measure various respiratory parameters. In the case of pressure support mode ventilation (PSV), assessment of the patient's work of breathing, which is the clinical parameter commonly used to infer the patient's effort per breath, is facilitated by evaluating the respiratory muscle pressure, $P_{mus}(t)$, over the breathing cycle. More specifically, the WoB is computed by integrating $P_{mus}(t)$ over the inhaled volume. For passive patient ventilation, it may be advantageous to verify that $P_{mus} \sim 0$ throughout the breathing cycle (indicating no appreciable WoB is being provided by the patient). Respiratory parameters such as respiratory resistance (R) and compliance (C) may also be of interest, or may need to be determined in order to assess other parameters.

Estimating $P_{mus}(t)$ in support modalities of mechanical ventilation enables the ventilator to be set such that the patient and ventilator share the mechanical work performed on the respiratory system. Quantitative assessment of $P_{mus}$ can be used to select the appropriate level of ventilation support in order to prevent both atrophy and fatigue of patient's respiratory muscles. The respiratory muscle pressure $P_{mus}(t)$ is typically assessed by measuring the esophageal pressure ($P_{es}$) via insertion of a balloon-tipped catheter in the patient's esophagus. The measured $P_{es}(t)$ is assumed to be a good proxy for the pleural pressure ($P_{pl}$) and can be used, in conjunction with an estimate of chest wall compliance $C_{cw}$, to compute the WoB via the so-called Campbell diagram or, equivalently, via explicit computation of $P_{mus}(t)$ and then of WoB.

Estimates of respiratory R and C are important per se, as they provide quantitative information to the physician about the mechanical properties of the patient's respiratory system and can be used to diagnose respiratory diseases and to select the appropriate ventilation modalities and therapeutic paths. Moreover, R and C can also be used to estimate $P_{mus}(t)$ as a non-invasive alternative to the use of the esophageal catheter. Assuming R and C are known, $P_{mus}(t)$ is suitably calculated by the following equation (known as the Equation of Motion of the Lungs):

$$P_y(t) = R\dot{V}(t) + \frac{V(t)}{C} + P_{mus}(t) + P_0 \qquad (1)$$

where $P_y(t)$ is the pressure measured at the Y-piece of the ventilator (also known as pressure at the mouth of the patient), $\dot{V}(t)$ is the flow of air into and out of the patient respiratory system (measured again at the Y-piece), $V(t)$ is the net volume of air delivered to the patient (measured by integrating the flow signal $\dot{V}(t)$ over time), and $P_0$ is a constant term to account for the pressure at the end of expiration.

In the case of a passive patient expending no breathing effort, it follows that $P_{mus}(t)=0$ throughout the breathing cycle and Equation (1) reduces to $$P_y(t) = R\dot{V}(t) + \frac{V(t)}{C} + P_0.$$

For the passive patient, $P_y(t)$, $\dot{V}(t)$, and $V(t)$ waveforms are fully determined by the selected ventilator settings and directly measurable, so that it is straightforward to generate a sufficient data set to determine R and C. By contrast, in the case of an active patient who is providing some WoB, the value of $P_{mus}(t)$ varies with time over the breath cycle, and Equation (1) is not easily solved.

For active patients, Equation (1) has generally been applied to non-invasively estimate $P_{mus}(t)$ using a two-step approach, where R and C are estimated first and then Equation (1) is applied to compute $P_{mus}(t)$ using the estimated values of R and C. Estimation of R and C may be performed by applying the flow-interrupter technique (also called End Inspiratory Pause, EIP). However, the flow-interrupter technique has the disadvantage of interfering with the ventilation pattern supplied to the patient. Moreover, the patient's respiratory muscles ought to be fully relaxed during the EIP maneuver in order for the computation of R and C to be valid, which may not always be the case. Another difficulty is that the values for R and C assessed via the EIP maneuver may be different from the R and C values attained during the ventilation pattern for which $P_{mus}(t)$ is to be determined. The EIP maneuver is performed in a specific ventilation mode (Volume Assisted Control, VAC) and the resulting R and C values might not be representative of the corresponding values that determine the dynamics of the lung mechanics under other ventilation modes, such as PSV, potentially leading to error in the subsequently computed $P_{mus}(t)$.

Another approach for estimating R and C in the case of an active patient is to apply least-squares fitting of Equation (1) to flow and pressure measurements under specific conditions for which the term $P_{mus}(t)$ is assumed to be zero. Some conditions for which $P_{mus}(t)$ could be assumed to be close to zero include: (1) periods of patient paralysis while Continuous Mandatory Ventilation (CMV) is applied; (2) periods of high Pressure Support Ventilation (PSV) levels; (3) specific portions of every pressure-supported breath that extend both during the inhalation and the exhalation phases; and (4) exhalation portions of pressure-supported breaths, where the flow signal satisfies specific conditions that are indicative of the absence of patient inspiratory efforts. However, Conditions (1) and (2) are undesirable clinical states that cannot be properly induced as an expedient for measuring R and C. The assumption of $P_{mus}(t)\sim 0$ for Condition (3) is questionable, especially during the inhalation phase. Condition (4) provides only a limited amount of data for the least squares fitting procedure. In sum, it has been difficult to attain a clinically useful period of sufficient time duration for which $P_{mus}(t)\sim 0$ is reliably achieved in an active patient in order to estimate R and C.

The following provides a new and improved system and method which overcome these problems and others A medical ventilator performs a method including: receiving measurements of pressure of air inspired by or expired from a ventilated patient operatively connected with the medical ventilator; receiving measurements of air flow into or out of the ventilated patient operatively connected with the medical ventilator; dividing a breath time interval into a plurality of fitting regions; and simultaneously estimating respiratory system's resistance and compliance or elastance, and respiratory muscle pressure by fitting to a time series of pressure and air flow samples in each region. In one approach, the fitting includes parameterizing the respiratory muscle pressure by a continuous differentiable function, such as a polynomial function, over the fitting region. In another approach, the fitting is to an equation of motion of the lungs in each region with monotonicity constraints of the respiratory muscle pressure and domain constraints of the respiratory parameters applied in each region.

One advantage resides in providing non-invasive estimation of respiratory parameters including resistance, compliance, and respiratory muscle pressure.

Another advantage resides in providing a ventilator with improved data analysis computational robustness.

Further advantages of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

FIG. 1 diagrammatically shows a ventilation system.

FIG. 2 diagrammatically shows a data analysis algorithm disclosed herein which simultaneously estimates multiple respiration parameters by approximating the respiratory muscle pressure $P_{mus}(t)$ by a low-order polynomial function.

Figure 3:
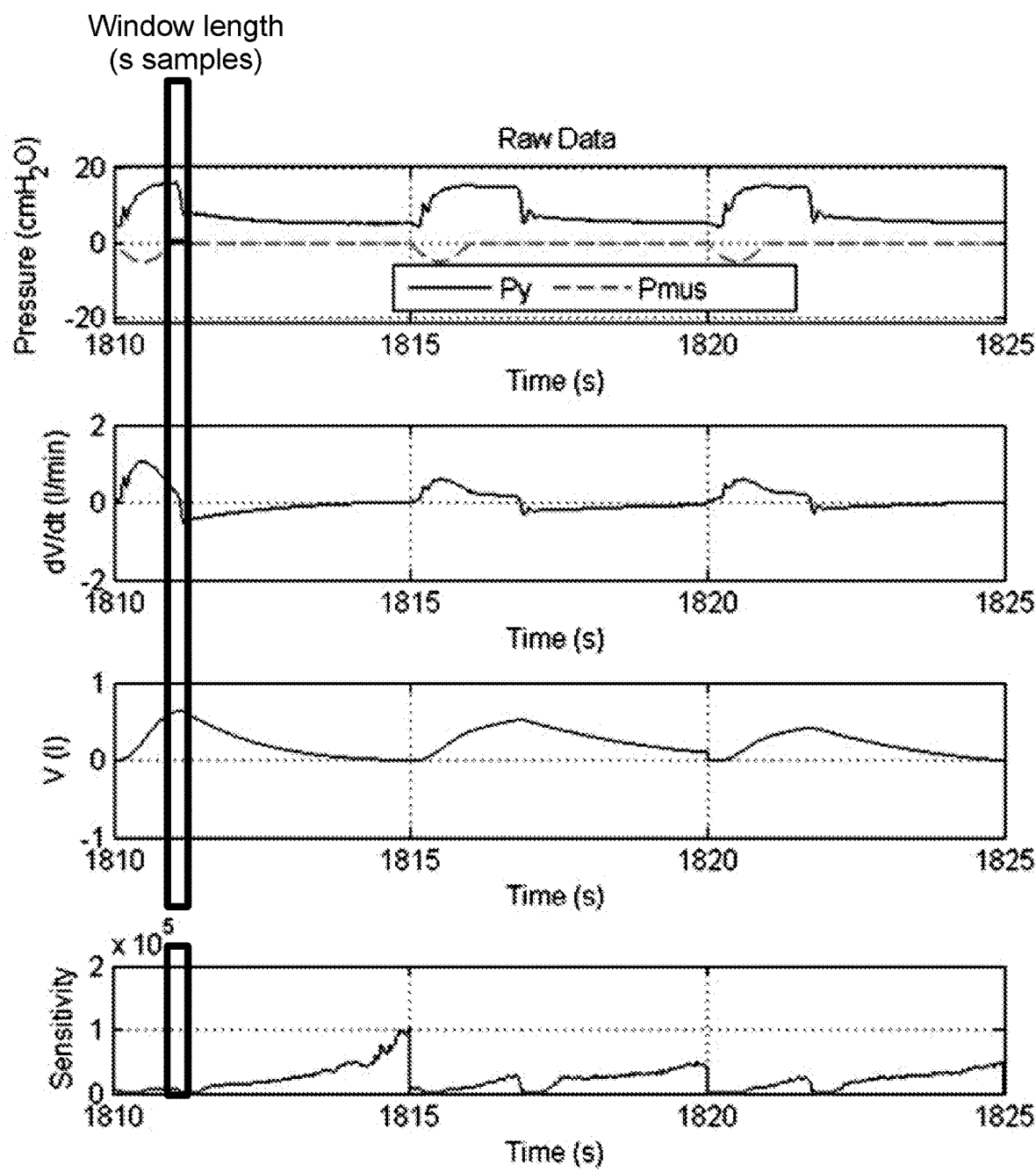

FIG. 3 plots simulated respiration waveforms over about three breaths, with sensitivity of the parameter matrix plotted in the lowermost plot of FIG. 3.

Figure 4:
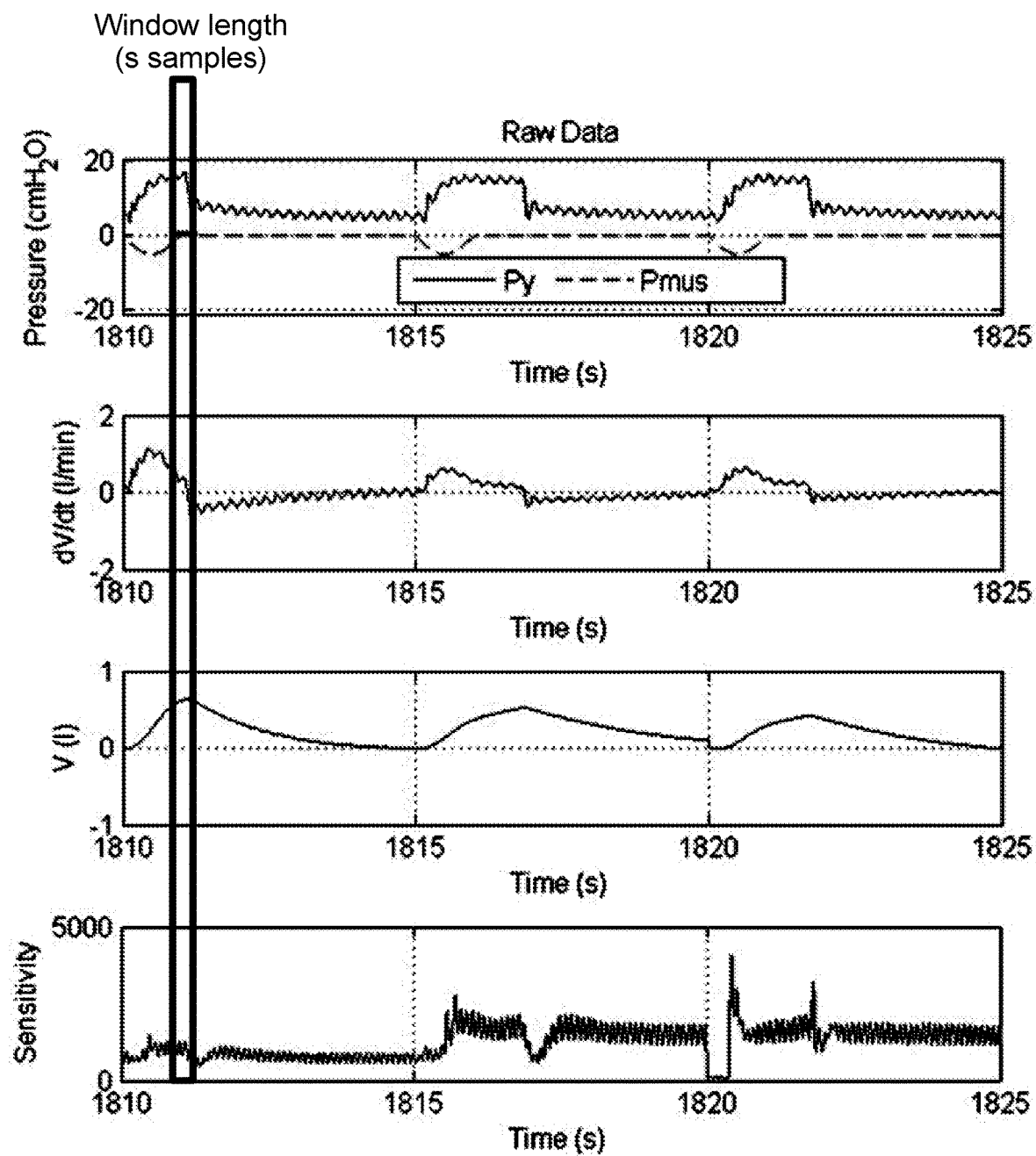

FIG. 4 plots simulated respiration waveforms over about three breaths with a small amplitude, high frequency pressure signal $\Delta P(t)$ superimposed on the ventilator-applied pressure, with sensitivity of the parameter matrix plotted in the lowermost plot of FIG. 4.

Figure 5:
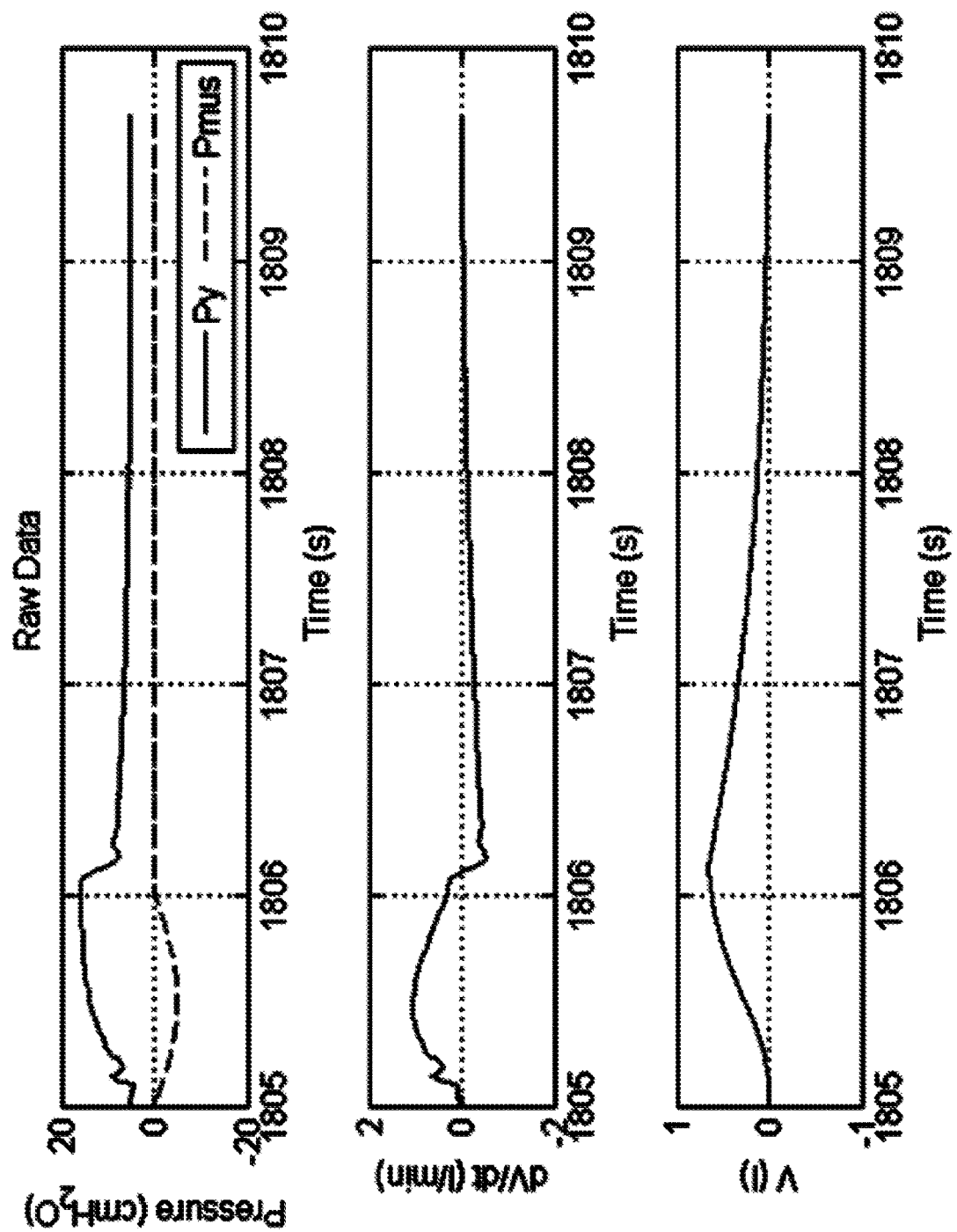

FIG. 5 plots normal interaction between the ventilator and a patient emulated using a computer-simulated Lung Emulator employing an ideal R, C circuit and no noise.

Figure 6:
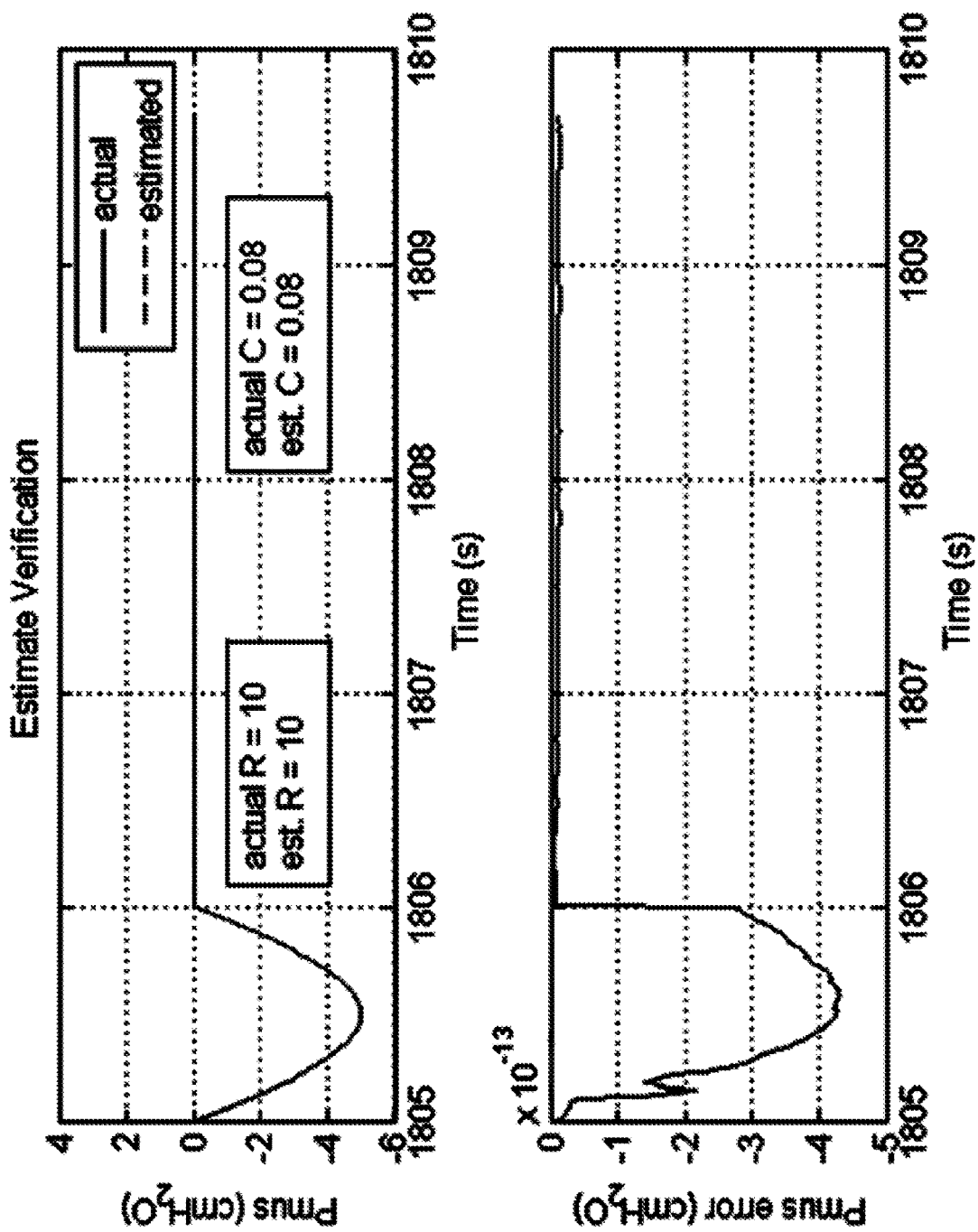

FIG. 6 plots the output of the disclosed constraint optimization algorithm (top plot) and the error (bottom plot) for the data of FIG. 5.

Figure 7:
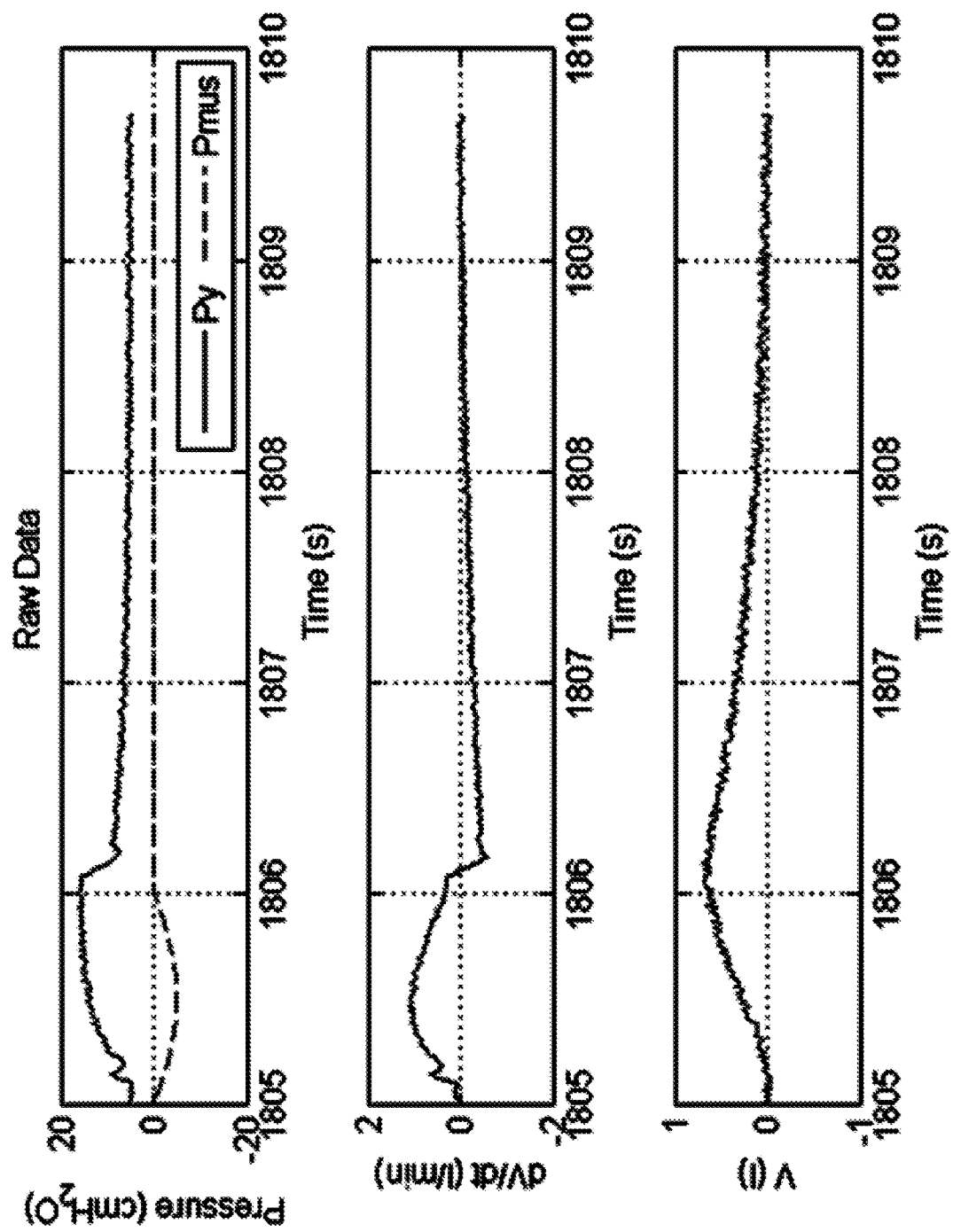

FIG. 7 plots normal interaction between the ventilator and a patient emulated using a computer-simulated Lung Emulator employing an ideal R, C circuit with numerically added noise.

Figure 8:
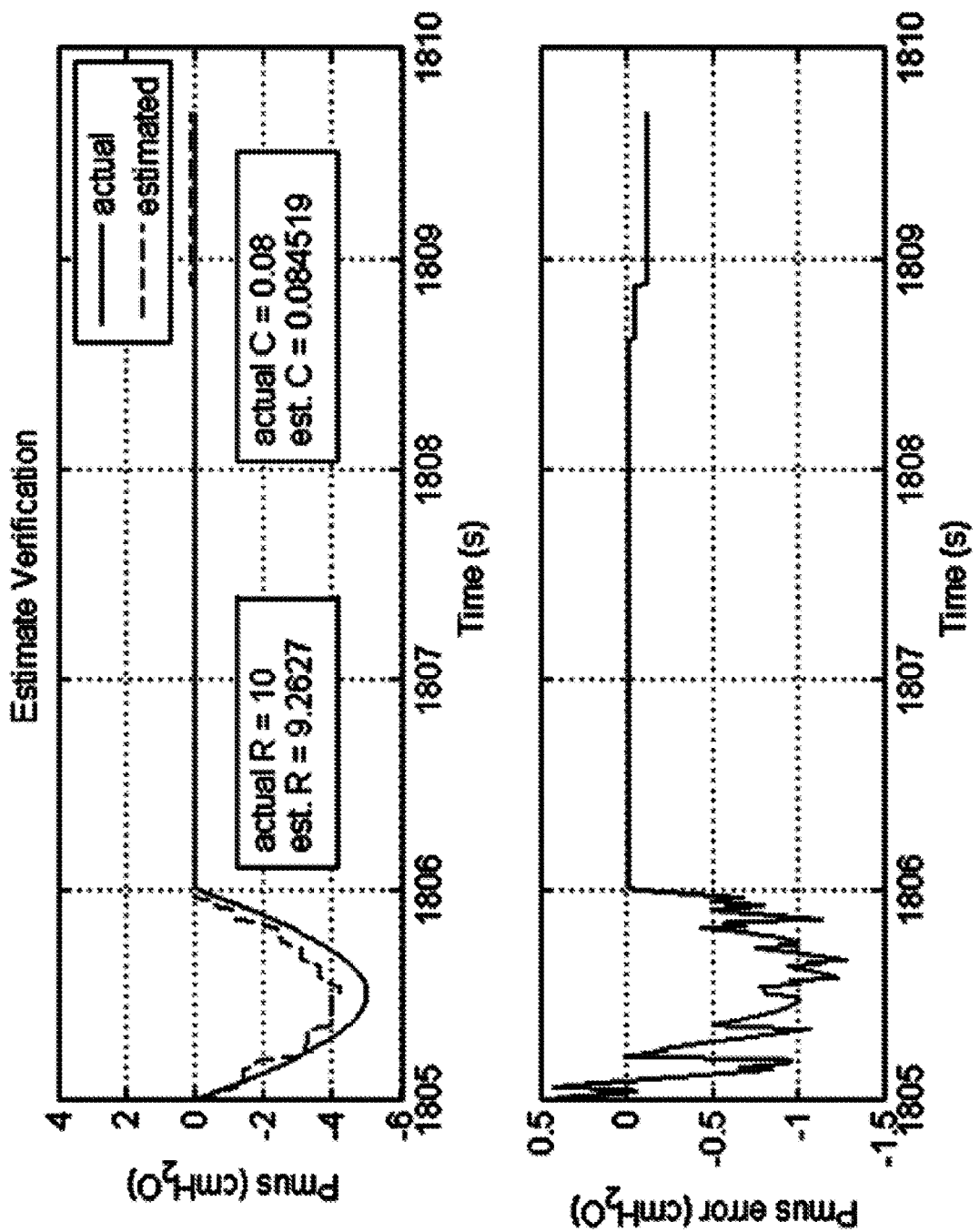

FIG. 8 plots the output of the disclosed constraint optimization algorithm (top plot) and the error (bottom plot) for the data of FIG. 7.

Figure 9:
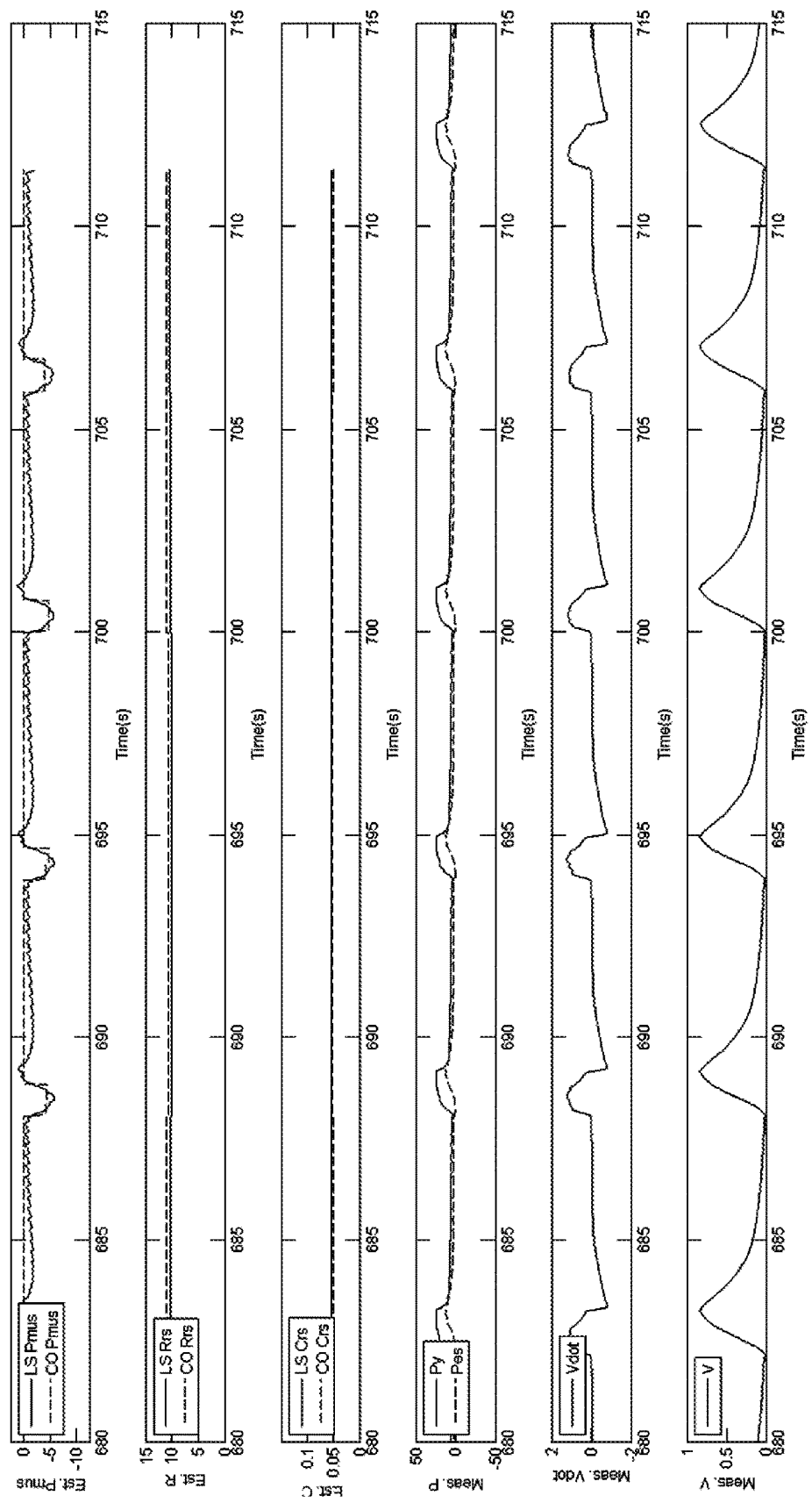
Figure 10:
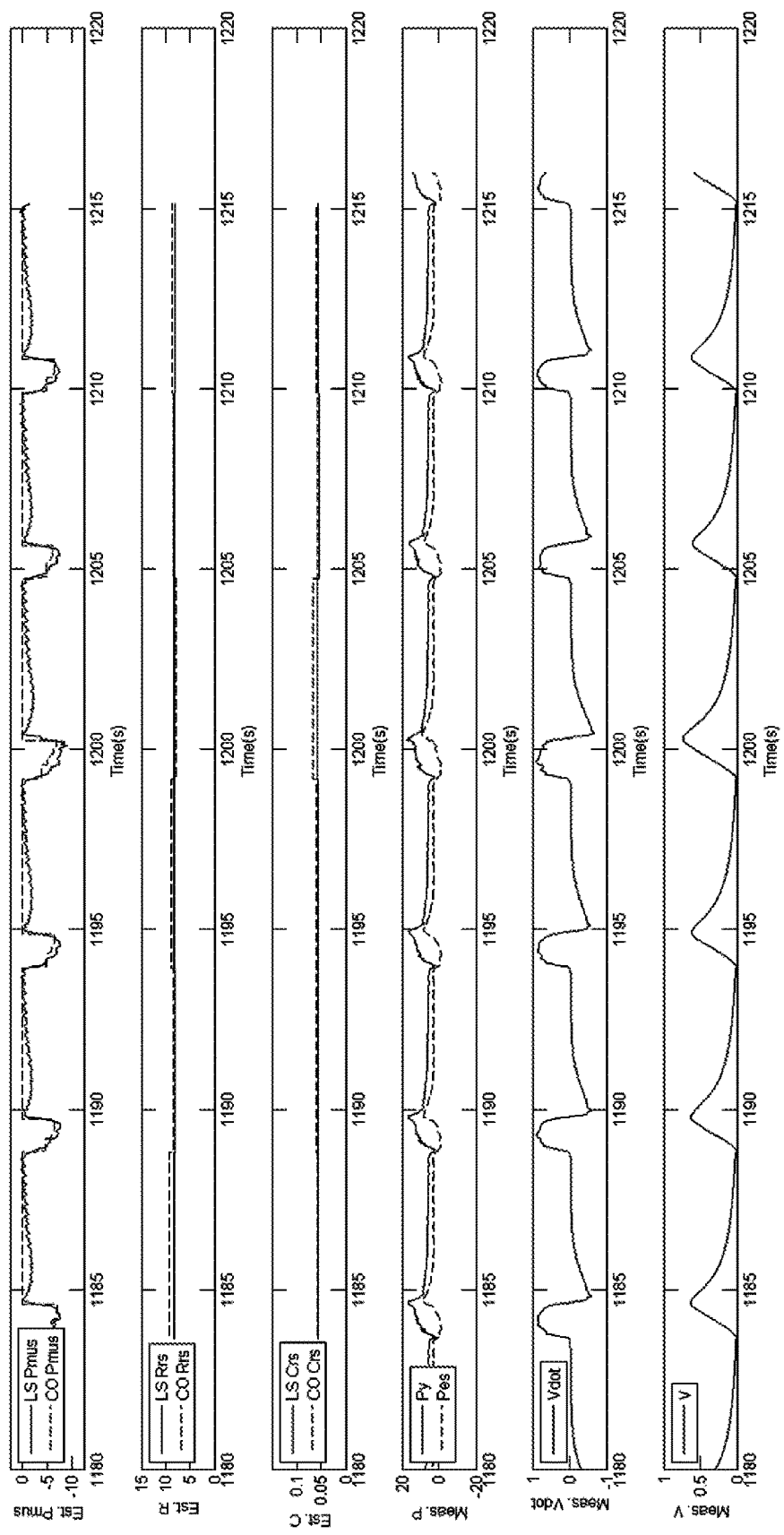

FIGS. 9 and 10 plot estimation of R, C, and $P_{mus}(t)$ of the output of the disclosed constraint optimization algorithm for a real pig (experimental data) under different pressure support ventilation (PSV) conditions: PSV=20 (FIG. 9) and PSV=10 (FIG. 10).

With reference to FIG. 1, a medical ventilator system includes a medical ventilator 10 that delivers air flow at positive pressure to a patient 12 via an inlet air hose 14. Exhaled air returns to the ventilator 10 via an exhalation air hose 16. A Y-piece 20 of the ventilator system serves to couple air from the discharge end of the inlet air hose 14 to the patient during inhalation and serves to couple exhaled air from the patient into the exhalation air hose 16 during exhalation. Note that the Y-piece is sometimes referred to by other nomenclatures, such as a T-piece 20. Not shown in FIG. 1 are numerous other ancillary components that may be provided depending upon the respiratory therapy being received by the patient 12. Such ancillary components may include, by way of illustration: an oxygen bottle or other medical-grade oxygen source for delivering a controlled level of oxygen to the air flow (usually controlled by the Fraction of Inspired Oxygen ($FiO_2$) ventilator parameter set by the physician or other medical personnel); a humidifier plumbed into the inlet line 14; a nasogastric tube to provide the patient 12 with nourishment; and so forth. The ventilator 10 includes a user interface including, in the illustrative example, a touch-sensitive display component 22 via which the physician, respiratory specialist, or other medical personnel can configure ventilator operation and monitor measured physiological signals and operating parameters of the ventilator 10. Additionally or alternatively, the user interface may include physical user input controls (buttons, dials, switches, et cetera), a keyboard, a mouse, audible alarm device(s), indicator light(s), or so forth.

With continuing reference to FIG. 1, in an upper portion some additional salient aspects of the ventilator system are diagrammatically illustrated in a block diagram format, including the ventilator 10 represented as a simplified block diagram, and the Y-piece 20 as a diagrammatic box with operative connections indicated by connecting arrows. In the illustrative example, the ventilator 10 is operating in a pressure support ventilation (PSV) mode as implemented by a controller 30. PSV is an appropriate ventilation mode for an active patient who is capable for expending at least some Work of Breathing (WoB) that is, whose diaphragm and other chest muscles are acting to at least assist in operating the lungs to perform breathing. In the PSV mode, the pressure provided by the ventilator 10 via the inlet air hose 14 operates together with the patient's WoB to perform the breathing. More generally, the controller 30 may implement various ventilation modes depending on the patient's condition and the therapy to be delivered. For example, in the case of a passive patient who is providing no WoB, the controller 30 may operate the ventilator 10 in a Pressure Control Ventilation (PCV) mode. (Note that in some classification schemes PSV is considered a type of PCV mode, since in both PCV and PSV the pressure applied by the ventilator 10 is a controlled parameter). Volume control ventilation modes are also sometimes used, although pressure limit settings may also be applied in volume control ventilation to guard against pulmonary barotrauma. In general, the ventilation controller 30 is implemented as a microprocessor with ancillary electronics such as read only memory (ROM), electronically erasable read only memory (EEPROM), flash memory, or another non-volatile memory component storing software or firmware executed by the microprocessor, random access memory (RAM) chip(s) to provide working memory, and so forth. If EEPROM, flash memory, or other updatable memory is used to store the software or firmware, then capabilities of the ventilator 10 can advantageously be updated (within the limits of its hardware components) by updating the software or firmware.

The PSV controller 30 outputs a desired pressure control signal as a function of time, which is used to control a ventilator compressor 32 (e.g. a pneumatic pump, turbopump, or so forth) that generates air flow at the controlled positive pressure that is applied to the Y-piece 20 via the inlet air hose 14. Depending upon the respiratory therapy to be provided, an oxygen regulator 34 may add a controlled fraction of oxygen to the air flow to achieve a Fraction of Inspired Oxygen ($FiO_2$) set by the physician, respiratory specialist, or other medical personnel who sets the configuration of the ventilator 10 for the patient 12. The pressure of the ventilatory pattern may vary during the breathing cycle to provide pressure-driven or pressure-assisted inhalation and to reduce pressure to facilitate exhalation.

The ventilator system typically further includes physiological monitoring sensors, such as an illustrative pressure sensor 40 and an illustrative flowmeter 42. The pressure sensor 40 measures the pressure at the Y-piece 20 (also known as pressure at the mouth of the patient), which is denoted here as $P_y(t)$. The flowmeter 42 measures the air flow rate into and out of the Y-piece 20, denoted herein as $\dot{V}(t)$. The flowmeter 42 also directly or indirectly provides the net volume of air delivered to the patient, denoted herein as $V(t)$, which may be directly measured or may be derived by integrating the flow rate $\dot{V}(t)$ over time. These measured values $P_y(t)$, $\dot{V}(t)$, $V(t)$, optionally along with other information such as the ventilator settings (e.g. $FiO_2$, the pressure profile delivered by the PSV control, et cetera) may be variously used by a ventilator monitor 44 to efficacy of the mechanical ventilation, to detect any deterioration of the state of the patient 12, to detect any malfunction of the ventilator 10, or so forth. As with the ventilator controller 30, the ventilator monitor 44 is implemented as a microprocessor with ancillary electronics, and may be updateable by updating the software or firmware. In some embodiments, the ventilator controller 30 and the ventilator monitor 44 may be implemented by a common microprocessor, and the controller and monitor functions may be integrated at various levels for example, it is contemplated to provide feedback-based ventilation control based on the measured values $P_y(t)$, $\dot{V}(t)$, $V(t)$ or parameters derived therefrom. Such software or firmware may be provided in the form of a non-transitory storage medium storing instructions readable and executable by the microprocessor of the ventilator monitor 44 to perform the monitoring functionality. The non-transitory storage medium may, for example, comprise a flash memory, optical disk, hard disk drive, or other storage medium.

Of salient interest here is assessment of the Work of Breathing (WoB), or of its derivative, the respiratory muscle pressure $P_{mus}(t)$. In general, WoB can be computed by integrating $P_{mus}(t)$ over the inhaled volume. In approaches disclosed herein, the assessment leverages the Equation of Motion of the Lungs given in Equation (1) herein, and hence the respiratory system's resistance R and compliance C are also salient parameters of interest. Equation (1) is evaluated with respect to a dataset of N data points measured over one or more breath cycles. Formally, the problem can be stated as follows:

$$Y = X\theta \quad (2)$$

where:
$Y = [P_y(1)\ P_y(2)\ \ldots\ P_y(N)]^T$ Pressure at Y-piece at times $1, \ldots, N$
$\dot{V} = [\dot{V}(1)\ \dot{V}(2)\ \ldots\ \dot{V}(N)]^T$ Flow rate at times $1, \ldots, N$
$V = [V(1)\ V(2)\ \ldots\ V(N)]^T$ Net air volume at times $1, \ldots, N$
$\theta = [R\ 1/C\ P_{mus}(1)\ P_{mus}(2)\ \ldots\ P_{mus}(N)]^T$ Parameters to be determined
and matrix X is an $(N+2) \times N$ matrix given by $X = [\dot{V}\ V\ I_N]$, where $I_N$ is an $N \times N$ identity matrix. By solving the system of equations $Y = X\theta$ for the parameter vector $\theta$, the resistance R, compliance C, and respiratory muscle pressure $P_{mus}(t)$ can be obtained. However, the system of equations represented by Equation (2) has more unknowns (N+2 unknowns) than equations (N equations), and hence is an underdetermined problem that cannot be solved because it has an infinite number of solutions, only one of which is the true "physical" solution.

Due to being underdetermined, the set of equations represented by matrix Equation (2) is very sensitive to measurement noise, unknown disturbances and unmodeled dynamics. Problematically, the noise is on the same time scale as the variations in the measured signals $P_y(t)$, $\dot{V}(t)$, $V(t)$ and in the fitted respiratory muscle pressure $P_{mus}(t)$. Thus, even if the underdetermined nature of the simultaneous estimation problem is somehow overcome, the resulting parameter values tend to be noisy and hence of limited clinical value.

With continuing reference to FIG. 1, it is disclosed herein to optionally counteract the effect of noise by superposing a relatively high-frequency and small-amplitude pressure signal, denoted as $\Delta P(t)$ herein, generated by a signal generator 50, onto the normal pressure profile supplied by the ventilator 10. As illustrated in FIG. 1, this can be done by adding a small-amplitude sinusoidal $\Delta P(t)$ to the controlled pressure signal output by the controller 30 using a signal combiner 52 prior to its input to the ventilator compressor 32. The amplitude of $\Delta P(t)$ is preferably chosen to be low enough to not appreciably impact the therapeutic value of the PSV signal output by the controller 30. The frequency of $\Delta P(t)$ is preferably high enough to be significantly higher than the breath frequency (e.g. typically a few breaths per minute corresponding to a frequency of, e.g., about 0.2 Hz for 5-sec breaths).

With continuing reference to FIG. 1, the underdeterminancy of the set of equations represented by matrix Equation (2) is addressed in embodiments disclosed herein (either with or without the optional superimposed $\Delta P(t)$) by solving Equation (2) in fitting region(s) 60 for which the respiratory muscle pressure $P_{mus}(t)$, although not assumed to be zero, is reasonably assumed to have some constraining characteristic(s) that enable the number of parameters to be reduced sufficiently to make Equation (2) overdetermined. The simultaneous estimation of the R, C and $P_{mus}(t)$ characterizing one breath (represented, without loss of generality, by N recorded time samples) by Equation (2) is an underdetermined problem, since it requires the computation of N+2 unknowns (N values for the N time samples of $P_{mus}(t)$, plus an additional unknown for R, and an additional unknown for C) from N equations corresponding to the N time samples. However, it is recognized herein that the N equations are not independent. Rather, it can be expected that the value of $P_{mus}(t)$ for neighboring samples should be continuous. In some regions, it may be reasonably assumed that $P_{mus}(t)$ is monotonically increasing, being flat, or monotonically decreasing.

In one embodiment, as disclosed herein, $P_{mus}(t)$ is approximated locally (that is, over a small number of samples s<N) by a $n^{th}$-order polynomial function suitably written as $P_{mus}(t)=a_0+a_1t+\ldots+a_nt^n$. This approximation is used to construct a least squares (LS) problem over a time window of s samples (where s<N) in which the unknowns are R, C, and $a_0, \ldots, a_n$. By keeping n+3<s (and in some embodiments n<<s), the underdeterminacy is overcome. The local approximation of $P_{mus}(t)$ by a polynomial is supported by the physiological intuition that $P_{mus}(t)$ is a smooth signal, with no abrupt discontinuities.

In another embodiment, the time interval covered by the N samples is divided into fitting regions in which $P_{mus}(t)$ is monotonically increasing, monotonically decreasing, or being flat over the entire fitting region. Within each region, a quadratic program can be constructed leveraging the known monotonicity in the region. This ensures efficient determination of a unique solution.

With reference now to FIG. 2, the first illustrative approach for overcoming the underdeterminancy of matrix Equation (2) is described in additional detail. In this approach the fitting regions 60 are chosen to be small enough for $P_{mus}(t)$ to be well-fitted by a polynomial approximation. The estimation of R, C, and $P_{mus}(t)$ at each time 1, . . . ,N is obtained by solving a LS problem over a window of lengths. For the usual case in which s<N, the window slides forward in time (that is, the window of width s is applied to successive increments of width s in the time series of samples 1, . . . ,N). In real-time patient monitoring, this can be done as a sliding window as each successive group of s samples are acquired, the fitting is performed so as to provide a real-time simultaneous estimate for R, C, $P_{mus}(t)$. The windows of width s can be non-overlapping; alternatively, it is contemplated for the neighboring windows of width s to overlap, which can provide a smoothing effect. FIG. 2 illustrates the case in which the polynomial approximation of $P_{mus}(t)$ over the time window of width s is of order n=2, that is, a polynomial: $P_{mus}(t)=a_0+a_1t+a_2t^2$. The matrix Equation (2) solved for the window of width s has the same form as Equation (2), but the parameters vector is different. To distinguish, the parameters vector is written as $\phi$ (rather than the parameters vector $\theta$ of Equation (2)), the matrix X is replaced by a matrix $\chi$, and the set of equations becomes:

$$Y=\chi\phi \quad (2a)$$

where:
$Y=[P_y(1)\ P_y(2)\ \ldots\ P_y(s)]^T$ For window of s samples
$\dot{V}=[\dot{V}(1)\ \dot{V}(2)\ \ldots\ \dot{V}(s)]^T$ For window of s samples
$V=[V(1)\ V(2)\ \ldots\ V(s)]^T$ For window of s samples
$\phi=[R\ 1/C\ a_0\ a_1\ \ldots\ a_n]^T$ Reduced to n+3 unknowns
and matrix $\chi$ is an s×(n+3) matrix given by:

$$\chi = \begin{pmatrix} \dot{V}(1) & V(1) & 1 & 1 & \ldots & s^n \\ \dot{V}(2) & V(2) & 1 & 2 & \ldots & s^n \\ \ldots & \ldots & \ldots & \ldots & \ldots & \ldots \\ \dot{V}(s) & V(s) & 1 & s & \ldots & s^n \end{pmatrix}$$

In the above notation, the first sample in the window of width s is designated without loss of generality as sample t=1, so that the last sample in the window is designated as sample t=s. Matrix Equation (2a) thus represents a set of s equations with n+3 unknowns, and is overdetermined so long as s>(n+3). More typically, s>>n. For example, in one illustrative example n=2 (quadratic approximation for $P_{mus}(t)$), the sampling rate is 100 Hz, and the window is 0.6 sec long corresponding to s=60.

Assuming an overdetermined set of equations, the matrix Equation (2a) can be solved in the least squares sense according to:

$$\phi=(\chi^T\chi)^{-1}\chi^T Y \quad (3)$$

Alternatively, an iterative least squares approximation approach such as gradient descent or Levenberg-Marquardt can be used to solve Equation (3) for the parameters $\phi$.

The illustrative approach employs a polynomial approximation of order n of $P_{mus}(t)$ over the time window of width s. The order n is chosen to be n≥2. Choosing a higher order provides the polynomial approximation with greater flexibility to represent changes in $P_{mus}(t)$ over the time window of width s; however, it also adds additional parameters (the total number of parameters is n+3) which makes the least squares fitting less robust. It is expected that n=2, n=3, or n=4 will be sufficient in most instances, although n>4 is also contemplated. Moreover, it will be appreciated that the approach can be generalized to approximating $P_{mus}(t)$ over the time window of width s by any continuous function that is smooth over the window of width s (i.e. that is differentiable over the window of width s). Other contemplated continuous and smooth approximation functions include spline functions, e.g. cubic spline functions.

With reference to FIGS. 3 and 4, the normal interaction between the ventilator and a patient is emulated using a computer-simulated Lung Emulator. This normal interaction gives rise to waveforms of flow and volume, plotted in FIG. 3, that make the data matrix ill-conditioned. Hence, the parameters estimated via Equation (3), are sensitive to noise or error in the measured data. In FIG. 3, the sensitivity of the parameter matrix is plotted in the lowermost plot of FIG. 3. Note in this plot that the sensitivity ordinate ranges [0, 200,000]. As previously described, this noise is optionally counteracted by superimposition of the low amplitude, high frequency component $\Delta P(t)$. To illustrate, FIG. 4 shows how the superposition of a sinusoidal signal $\Delta P(t)$ of small-amplitude (1 $cmH_2O$ in this example) and relatively high-frequency (5 Hz in this example) significantly reduces the sensitivity (condition number) of the parameter matrix, thus improving the robustness against noise. Note that in FIG. 4 the lowermost sensitivity plot has a sensitivity ordinate range of only [0, 5000]. To implement $\Delta P(t)$, the signal generator 50 and signal combiner 52 (see FIG. 1) can be implemented in software or firmware as part of the software or firmware of the ventilator controller 30, or the signal generator 50 and signal combiner 52 can be components separate from the ventilator controller 30, e.g. a voltage-controlled oscillator (VCO) circuit outputting the signal $\Delta P(t)$, and an op-amp-based signal combiner or other signal combiner implemented in hardware.

The approach of fitting $P_{mus}(t)$ to a smooth, continuous function (e.g. a polynomial of order n≥2) as described with reference to FIG. 2 has a further advantage of operating in the time domain, and hence enabling the respiratory data analysis to readily incorporate a non-linear model of the lung mechanics. For example, it is not necessary to assume that R and C are constant values over the breath cycle. In one illustrative approach for taking into account possible non-linearities in the resistance R and the compliance C, Equation (1) can be modified to have quadratic characteristics as follows:

$$P_y(t) = (R_0 + R_1 \cdot |\dot{V}(t)|)\dot{V}(t) + \left(\frac{1}{C_0} + \frac{V(t)}{C_1}\right)V(t) + P_{mus}(t) + P_0 \quad (4)$$

Equation (4) is characterized by a flow-dependent resistance $R_0+R_1\cdot|\dot{V}(t)|$ and a volume-dependent elastance $$\left(\frac{1}{C_0} + \frac{V(t)}{C_1}\right).$$

The parameters to be estimated are now $R_0$, $R_1$, $C_0$, $C_1$, and $P_{mus}(t)$. The least squares (LS) problem to be solved (with polynomial approximation of $P_{mus}(t)$, i.e. corresponding to Equation (2a)) becomes:

$$Y = \chi_{NL}\phi_{NL} \quad (5)$$

where:
$Y=[P_y(1)\ P_y(2)\ \ldots\ P_y(s)]^T$
$\dot{V}_0=[\dot{V}(1)\ \dot{V}(2)\ \ldots\ \dot{V}(s)]^T$
$\dot{V}_1=[\dot{V}(1)|\dot{V}(1)|\ \dot{V}(2)|\dot{V}(2)|\ \ldots\ \dot{V}(s)|\dot{V}(s)|]^T$
$V_0=[V(1)\ V(2)\ \ldots\ V(s)]^T$
$V_1=[V^2(1)\ V^2(2)\ \ldots\ V^2(s)]^T$
$\phi[R_0\ R_1\ 1/C_0\ 1/C_1\ a_0, a_1\ \ldots\ a_n]^T$
and matrix $\chi$ is an s×(n+5) matrix given by:

$$\chi = \begin{pmatrix} \dot{V}_0(1) & \dot{V}_1(1) & V_0(1) & V_1(1) & 1 & 1 & \ldots & 1^n \\ \dot{V}_0(2) & \dot{V}_1(2) & V_0(2) & V_1(2) & 1 & 2 & \ldots & 2^n \\ \ldots & \ldots & \ldots & \ldots & \ldots & \ldots & \ldots & \ldots \\ \dot{V}_0(s) & \dot{V}_1(s) & V_0(s) & V_1(s) & 1 & s & \ldots & s^n \end{pmatrix}$$

Assuming an overdetermined set of equations, the matrix Equation (5) can be solved in the least squares sense according to:

$$\phi_{NL} = (\chi_{NL}^T\chi_{NL})^{-1}\chi_{NL}^T Y \quad (6)$$

Alternatively, an iterative least squares approximation approach such as gradient descent or Levenberg-Marquardt can be used to solve Equation (5) for the parameters $\phi_{NL}$.

In the following, the second illustrative approach for overcoming the underdeterminancy of matrix Equation (2) is described in additional detail. In this approach each fitting region 60 is chosen so that $P_{mus}(t)$ is monotonic (either monotonically increasing, or monotonically decreasing) in the entire fitting region. In this approach, inequality constraints on the possible values of $P_{mus}(t)$, and domain constraints that R and C can take are introduced based on physiological considerations, such that the least squares (LS) solution becomes unique. In a suitable approach, the constraints are cast in linear form and define an objective function to be minimized of LS type, so that the mathematical formulation of the optimization problem to be solved falls into the category of quadratic programming. Not only is the uniqueness of solution now guaranteed, but also the routine to solve the program can be very efficient since quadratic programming is a mature mathematical technology.

Optionally, robustness of the resulting method to estimate R, C, and $P_{mus}(t)$ is further improved by the introduction of equality constraints. Robustness is advantageous for practical applications due to uncertainties and non-ideal factors that can affect the application (measurement noise, unknown disturbances, nonlinearities, unmodeled dynamics). Equality constraints on the values of $P_{mus}(t)$ are used to reduce the number of unknowns to describe $P_{mus}(t)$, hence making the overall estimation more robust.

With reference to FIG. 5, the normal interaction between the ventilator and a patient is emulated using a computer simulated Lung Emulator. As seen in FIG. 5, topmost plot, over a single breath draw (corresponding to time 1805-1806 sec in illustrative FIG. 5), $P_{mus}(t)$ is first monotonically decreasing (toward more negative values as the diaphragm and chest muscles operate to create negative respiratory muscle pressure to draw air into the lungs), and then $P_{mus}(t)$ transitions to a monotonically increasing region as the negative respiratory muscle pressure is reduced gradually to $P_{mus}(t)=0$ as the breath draw is completed. As seen in FIG. 5, topmost plot, $P_{mus}(t)=0$ generally holds between breath draws as exhalation is driven by relaxation of the expanded lungs.

In view of these observations, the approach involves defining a monotonically decreasing region and a monotonically increasing region, and translating the monotonicity into mathematical inequalities to constrain the least squares optimization. The objective function to be minimized, denoted herein as J, is readily derived from Equation (1):

$$J = \Sigma_{t=1}^{N}(P_y(t) - R\dot{V}(t) - EV(t) - P_{mus}(t))^2 \quad (7)$$

In the objective J of Equation (7), the respiratory system's compliance C is replaced by the elastance E according to the relationship $$E = \frac{1}{C}.$$

The objective function J is minimized with respect to the parameters R, C (or E), and $P_{mus}(1), \ldots, P_{mus}(N)$, subject to inequality constraints capturing the known monotonic regions of $P_{mus}(t)$. This problem can be cast as a quadradic program by minimizing J subject to the following inequality constraints:

$$P_{mus}(2) \leq P_{mus}(1) \quad (8)$$
$$P_{mus}(3) \leq P_{mus}(2)$$
$$\ldots$$
$$P_{mus}(m-1) \leq P_{mus}(m-2)$$
$$P_{mus}(m) \leq P_{mus}(m-1)$$
$$P_{mus}(m) \leq P_{mus}(m+1)$$
$$P_{mus}(m+1) \leq P_{mus}(m+2)$$
$$\ldots$$
$$P_{mus}(N-1) \leq P_{mus}(N)$$

where the time t=m is the "turning point", that is, the point at which $P_{mus}(t)$ goes from being monotonically decreasing (for t=1, ..., m) to being monotonically increasing (for t=m+1, ...,N). Said another way, $P_{mus}(m)$ is the time at which $P_{mus}(t)$ reaches its minimum value. Optionally, the quadratic program can include additional constraints based on physiological knowledge. For example, if there is some known minimum respiratory muscle pressure $P_{min}$ and/or some known maximum respiratory muscle pressure $P_{max}$ (for example, it may in some instances be assumed that $P_{max}=0$ as the diaphragm and chest muscles cannot act to apply positive pressure to the lungs), then the following inequalities can be added:

$$P_{min} \le P_{mus}(1) \le P_{max} \qquad (9)$$
$$P_{min} \le P_{mus}(2) \le P_{max}$$
$$\dots$$
$$P_{min} \le P_{mus}(N) \le P_{max}$$

Similar limit (domain) constraints may optionally be placed on R and C:

$$R_{min} \le R \le R_{max} \qquad (10)$$
$$E_{min} \le E \le E_{max}$$

Eigenvalue decomposition of the quadratic matrix that can be constructed from the objective function using real data demonstrates that the problem is fully determined under Constraints (8)-(10). All the eigenvalues are negative but two, which are zero. For the quadratic problem to have a unique solution all the eigenvalues should be strictly negative. The eigenvectors associated with the zero eigenvalues are, however, minimizing directions forbidden by the given constraints, so that the underdeterminacy of the LS simultaneous estimation of R, C, and $P_{mus}(t)$ is overcome.

The foregoing formulation assumes that the time t=m at which the monotonicity of $P_{mus}(t)$ switches is known. However, this is not the case in real applications. To determine switch time m, a search of the optimal monotonicity switch time can be performed, by solving the quadratic program defined by objective J (Equation (7)) and Constraints (8)-(10) for each candidate minimum time and choosing the candidate minimum time that yields the smallest value for J as the minimum time m.

Constraints in addition to, or instead of, the Constraints (8)-(10) are contemplated. The input to the algorithm is the set of measured $P_y(t)$, $\dot{V}(t)$, and $V(t)$ over a complete breath, where again $V(t)$ is suitably obtained by integration of $\dot{V}(t)$. The output includes a value for each of R, C (or E), and the waveform $P_{mus}(t)$ for the entire breath.

With reference to FIGS. 5-8, experiments on simulated respiratory data indicate that the above-described quadratic program algorithm provides suitable estimates of R, C and $P_{mus}(t)$ when the pressure and flow data come from an ideal R, C circuit with and without additive noise corrupting the measurements. FIG. 5 shows the simulated respiration data for the ideal R, C circuit simulator with no noise in the signals, while FIG. 6 shows the output of the quadratic program algorithm (top plot) and the error (bottom plot; note that the ordinate of the error plot has a range $[0, 10^{-13}]$ so that negligible error is observed throughout). FIGS. 7 and 8 show the same experiment as FIGS. 5 and 6, but this time with numerically-generated noise added. While some error is observed due to the noise, the fit is still fairly accurate.

To provide even further improvement, the disclosed techniques can be combined, e.g. the quadratic program (Equation (7) with Constraints (8)-(10)) can be performed in conjunction with a parameterization of $P_{mus}(t)$, for example as described with reference to FIG. 2 or some other parameterization.

With reference to FIGS. 9 and 10, estimation of R, C, and $P_{mus}(t)$ for a real pig (experimental data) is presented, under different pressure support ventilation (PSV) conditions: PSV=20 (FIG. 9) and PSV=10 (FIG. 10). These data show how the quadratic program algorithm can non-invasively replicate the values of resistance and compliance invasively estimated on a pig via an esophageal catheter. The dashed lines represent the estimates obtained by the quadratic program with additional parameterization in which $P_{mus}(t)$ is parameterized via four regions, three of which regions were characterized each by a slope to be estimated, and the fourth region with monotonicity constraint and a negative peak time to be estimated. The solid lines are the LS estimates of R and C obtained by measuring $P_{es}(t)$, which requires an invasive catheter (knowledge of $P_{es}(t)$ permits estimation of resistance and compliance of the respiratory system via LS, with no underdeterminacy issues). The quadratic program algorithm is therefore able to provide non-invasively the same R and C estimates that the current state-of-the-art obtains invasively.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A medical ventilator system comprising:
a ventilator configured to deliver an air flow at positive pressure to a ventilated patient;
a pressure sensor configured to measure pressure $P_y(t)$ of air inspired by or expired from ventilated patient;
a flowmeter configured to measure air flow $\dot{V}(t)$ into or out of the ventilated patient; and
a ventilator monitor comprising a microprocessor programmed to estimate respiratory muscle pressure during breathing by dividing the breath time interval into a plurality of fitting regions and simultaneously estimating respiratory system's resistance R and compliance C or elastance E, and respiratory muscle pressure $P_{mus}(t)$ in each region by fitting to a time series of $P_y(t)$ and $\dot{V}(t)$ samples in that region, wherein an equation of motion of the lungs is fitted in each fitting region with monotonicity constraints applied to the respiratory muscle pressure $P_{mus}(t)$ in each fitting region, and a normal interaction between the ventilator and the ventilated patient based upon the equation of motion of the lungs is displayed on a computer-simulated lung emulator.

2. The medical ventilator system of claim 1 wherein the ventilator monitor is programmed to simultaneously estimate the respiratory system's resistance and the compliance or elastance, and the respiratory muscle pressure in each fitting region by operations including:
fitting respiratory muscle pressure $P_{mus}(t)$ parameterized by a continuous differentiable function over the fitting region.

3. The medical ventilator system of claim 2, wherein the continuous differentiable function is a polynomial or spline function.

4. The medical ventilator system of claim 2, wherein the continuous differentiable function is a polynomial function of the form:

$$P_{mus}(t)=a_0+a_1 t+\dots+a_n t^n$$

and the simultaneous fitting includes estimating the parameters $a_0, a_1, \dots, a_n$.

5. The medical ventilator system of claim 1, wherein the fitting regions include a first region within which a monotonically decreasing constraint of the respiratory muscle pressure $P_{mus}(t)$ is applied and a second region after the first region in time within which a monotonically increasing constraint is applied.

6. The medical ventilator system of claim 1, wherein the simultaneous estimation of respiratory system's resistance R and compliance C or elastance E, and respiratory muscle pressure $P_{mus}(t)$ in each fitting region by fitting to a time series of $P_y(t)$ and $\dot{V}(t)$ samples comprises:
   solving an equation of motion of the lungs in each fitting region given by:

$$P_y(t) = R\dot{V}(t) + \frac{V(t)}{C} + P_{mus}(t) + P_0$$

or $$P_y(t) = R\dot{V}(t) + EV(t) + P_{mus}(t) + P_0$$

where V(t) is a net volume of air delivered to the patient computed by integrating the air flow $\dot{V}(t)$ and $P_0$ is a constant.

7. The medical ventilator system of claim 1, wherein the simultaneous estimation of respiratory system's resistance R and compliance C or elastance E, and the respiratory muscle pressure $P_{mus}(t)$ in each fitting region by fitting to a time series of $P_y(t)$ and $\dot{V}(t)$ samples comprises:
   solving an equation of motion of the lungs in each fitting region given by:

$$P_y(t) = (R_0 + R_1 \cdot |\dot{V}(t)|)\dot{V}(t) + \left(\frac{1}{C_0} + \frac{V(t)}{C_1}\right)V(t) + P_{mus}(t) + P_0$$

or $$P_y(t) = (R_0 + R_1 \cdot |\dot{V}(t)|)\dot{V}(t) + (E_0 + E_1 V(t))V(t) + P_{mus}(t) + P_0$$

where V(t) is a net volume of air delivered to the patient computed by integrating the air flow $\dot{V}(t)$ and $P_0$ is a constant and respiratory system's resistance $R=R_0+R_1 \cdot |\dot{V}(t)|$ and compliance $$C = \frac{1}{C_0} + \frac{V(t)}{C_1}$$

or chest wall elastance $E=E_0+E_1 V(t)$.

8. A non-transitory storage medium storing instructions readable and executable by one or more microprocessors of a medical ventilator to cause the medical ventilator to perform a method comprising:
   instructions for receiving measurements of pressure $P_y(t)$ of air inspired by or expired from a ventilated patient operatively connected with the medical ventilator;
   instructions for receiving measurements of air flow $\dot{V}(t)$ into or out of the ventilated patient operatively connected with the medical ventilator;
   instructions for dividing a breath time interval into a plurality of fitting regions;
   instructions for simultaneously estimating respiratory system's resistance R and a compliance C or elastance E, and respiratory muscle pressure $P_{mus}(t)$ in each fitting region by fitting to a time series of $P_y(t)$ and $\dot{V}(t)$ samples in that fitting region; and
   instructions for fitting an equation of motion of the lungs in each fitting region with monotonicity constraints applied to the respiratory muscle pressure $P_{mus}(t)$ in each fitting region; and instructions for displaying a normal interaction between the ventilator and the ventilated patient based upon the fitted equation of motion of the lungs on a computer-simulated lung emulator.

9. The non-transitory storage medium of claim 8, further comprising:
   instructions for fitting respiratory muscle pressure $P_{mus}(t)$ parameterized by a continuous differentiable function over the fitting region.

10. The non-transitory storage medium of claim 8, further comprising:
    instructions for fitting parameters $a_0, a_1, \ldots, a_n$ of respiratory muscle pressure $P_{mus}(t)$ parameterized according to the polynomial approximation:

$$P_{mus}(t)=a_0+a_1 t+ \ldots +a_n t^n.$$

11. The non-transitory storage medium of claim 10, where n is two or three.

12. The non-transitory storage medium of claim 8, wherein the fitting regions include a first region within which a monotonically decreasing constraint is applied to the respiratory muscle pressure $P_{mus}(t)$ and a second region after the first region in time within which a monotonically increasing constraint is applied to the respiratory muscle pressure $P_{mus}(t)$.

13. The non-transitory storage medium of claim 12, further comprising:
    instructions for solving a quadratic program including an objective function representing the equation of motion of the lungs and a set of inequalities relating samples of the respiratory muscle pressure $P_{mus}(t)$ so as to define the monotonicity constraints.

14. A method comprising:
    receiving measurements of pressure $P_y(t)$ of air inspired by or expired from a ventilated patient;
    receiving measurements of air flow $\dot{V}(t)$ into or out of the ventilated patient;
    dividing a breath time interval into a plurality of fitting regions; and
    in each fitting region, solving:

$$P_y(t) = R\dot{V}(t) + \frac{V(t)}{C} + P_{mus}(t) + P_0$$

or $$P_y(t) = R\dot{V}(t) + EV(t) + P_{mus}(t) + P_0$$

where V(t) is a net volume of air delivered to the patient computed by integrating the air flow $\dot{V}(t)$ and $P_0$ is a constant, in order to simultaneously estimate respiratory system's resistance R and compliance C or elastance E, and respiratory muscle pressure $P_{mus}(t)$ in each fitting region by fitting to a time series of $P_y(t)$ and $\dot{V}(t)$ samples in that fitting region;
    fitting an equation of motion of the lungs in each fitting region with monotonicity constraints applied to the respiratory muscle pressure $P_{mus}(t)$ in each fitting region; and
    displaying a normal interaction between the ventilator and the ventilated patient based upon the fitted equation of motion of the lungs on a computer-simulated lung emulator.

15. The method of claim 14, wherein:
respiratory system's resistance $R=R_0+R_1 \cdot |\dot{V}(t)|$ and
respiratory system's compliance $$C = \frac{1}{C_0} + \frac{V(t)}{C_1}$$

or elastance $E=E_0+E_1 V(t)$.

16. The method of claim 14, wherein the solving further comprises:
   parameterizing respiratory muscle pressure $P_{mus}(t)$ by a continuous differentiable function over the fitting region.

17. The method of claim 16, wherein the continuous differentiable function over the fitting region is $P_{mus}(t)=a_0+a_1 t+ \ldots +a_n t^n$ to and the solving further comprises:
   simultaneously estimating respiratory system's resistance R and compliance C or elastance E, and parameters $a_0, a_1, \ldots, a_n$ in each fitting region by fitting to a time series of $P_y(t)$ and $\dot{V}(t)$ samples in that fitting region.

18. The method of claim 14, wherein the monotonicity constraints are defined by a set of inequalities relating samples of the respiratory muscle pressure $P_{mus}(t)$ in the fitting region.

* * * * *